United States Patent
Belson et al.

(10) Patent No.: US 8,313,508 B2
(45) Date of Patent: Nov. 20, 2012

(54) BIOPSY INCISION CLOSURE DEVICE

(75) Inventors: Amir Belson, Los Altos, CA (US); Eric Storne, Menlo Park, CA (US); Brian Beckey, Woodside, CA (US)

(73) Assignee: Zipline Medical, Inc., Los Altos, CA (US)

( * ) Notice: Subject to any disclaimer, the term of this patent is extended or adjusted under 35 U.S.C. 154(b) by 0 days.

(21) Appl. No.: 13/286,378

(22) Filed: Nov. 1, 2011

(65) Prior Publication Data

US 2012/0046691 A1   Feb. 23, 2012

Related U.S. Application Data

(63) Continuation of application No. 13/096,602, filed on Apr. 28, 2011.

(60) Provisional application No. 61/343,916, filed on May 3, 2010, provisional application No. 61/397,604, filed on Jun. 14, 2010, provisional application No. 61/462,329, filed on Feb. 1, 2011.

(51) Int. Cl.
*A61B 17/08* (2006.01)
*A61D 1/00* (2006.01)

(52) U.S. Cl. ...................................... 606/216
(58) Field of Classification Search .................. 606/216
See application file for complete search history.

(56) References Cited

U.S. PATENT DOCUMENTS

| | | | |
|---|---|---|---|
| 2,012,755 A | 8/1935 | Muth | |
| 2,747,248 A | 5/1956 | Mercer | |
| 3,487,836 A * | 1/1970 | Niebel et al. .......... 606/216 |
| 3,516,409 A | 6/1970 | Howell | |
| 3,863,640 A | 2/1975 | Haverstock | |
| 3,926,193 A | 12/1975 | Hasson | |
| 3,933,158 A | 1/1976 | Haverstock | |
| 3,971,384 A * | 7/1976 | Hasson .......... 606/218 |
| 4,038,989 A | 8/1977 | Romero-sierra et al. | |
| 4,114,624 A | 9/1978 | Haverstock | |
| 4,526,173 A | 7/1985 | Sheehan | |
| 4,535,772 A | 8/1985 | Sheehan | |
| 4,605,005 A | 8/1986 | Sheehan | |
| 4,676,245 A | 6/1987 | Fukuda | |
| 4,881,546 A | 11/1989 | Kaessmann | |
| 4,905,694 A | 3/1990 | Will | |
| 4,976,726 A | 12/1990 | Haverstock | |

(Continued)

FOREIGN PATENT DOCUMENTS

WO    WO 2011/043786 A1    4/2011

OTHER PUBLICATIONS

U.S. Appl. No. 13/096,602, filed Apr. 28, 2011, Belson et al.

(Continued)

*Primary Examiner* — Melanie Tyson
(74) *Attorney, Agent, or Firm* — Wilson, Sonsini, Goodrich & Rosati

(57) ABSTRACT

A biopsy incision closure device includes a base having a frame incorporated therein. Together, the base and frame define an opening for performing a biopsy incision when the device is placed over a tissue surface. The base is typically composed of an elastomeric material and the frame comprises resilient inelastic members which can be used to close the opening in a highly uniform manner with minimum distortion and stress introduced into the tissue edges being drawn together.

18 Claims, 9 Drawing Sheets

U.S. PATENT DOCUMENTS

| | | | |
|---|---|---|---|
| 5,377,695 | A | 1/1995 | An Haack |
| 5,514,155 | A | 5/1996 | Daneshvar |
| 5,665,108 | A | 9/1997 | Galindo |
| 6,126,615 | A | 10/2000 | Allen et al. |
| 6,176,868 | B1 | 1/2001 | Detour |
| 7,455,681 | B2 | 11/2008 | Wilke et al. |
| 7,645,285 | B2 * | 1/2010 | Cosgrove et al. ............ 606/151 |
| 2005/0020956 | A1 | 1/2005 | Lebner |
| 2005/0234485 | A1 | 10/2005 | Seegert et al. |
| 2006/0200198 | A1 | 9/2006 | Riskin et al. |
| 2007/0026078 | A1 | 2/2007 | Almarsson et al. |
| 2007/0088339 | A1 | 4/2007 | Luchetti |
| 2007/0141130 | A1 | 6/2007 | Villanueva et al. |
| 2007/0260278 | A1 | 11/2007 | Wheeler et al. |
| 2008/0033334 | A1 | 2/2008 | Gurtner et al. |
| 2008/0081951 | A1 | 4/2008 | Frasier et al. |
| 2008/0114396 | A1 | 5/2008 | Cory et al. |
| 2008/0287864 | A1 | 11/2008 | Rosenberg |
| 2009/0036922 | A1 | 2/2009 | Riskin et al. |
| 2009/0099496 | A1 | 4/2009 | Heegaard et al. |
| 2009/0299255 | A1 | 12/2009 | Kazala et al. |
| 2009/0299257 | A1 | 12/2009 | Long et al. |
| 2009/0299303 | A1 | 12/2009 | Seegert |
| 2010/0121286 | A1 | 5/2010 | Locke et al. |
| 2010/0280545 | A1 * | 11/2010 | Fridman ...................... 606/213 |

OTHER PUBLICATIONS

International search report and written opinion dated Jul. 29, 2011 for PCT/US2011/034649.
U.S. Appl. No. 13/286,757, filed Nov. 1, 2011, Belson et al.
U.S. Appl. No. 13/414,176, filed Mar. 7, 2012, Belson et al.
International search report and written opinion dated Oct. 21, 2011 for PCT Application No. US2011/40213.
International search report dated Jul. 30, 2010 for PCT/US2010/000430.

* cited by examiner

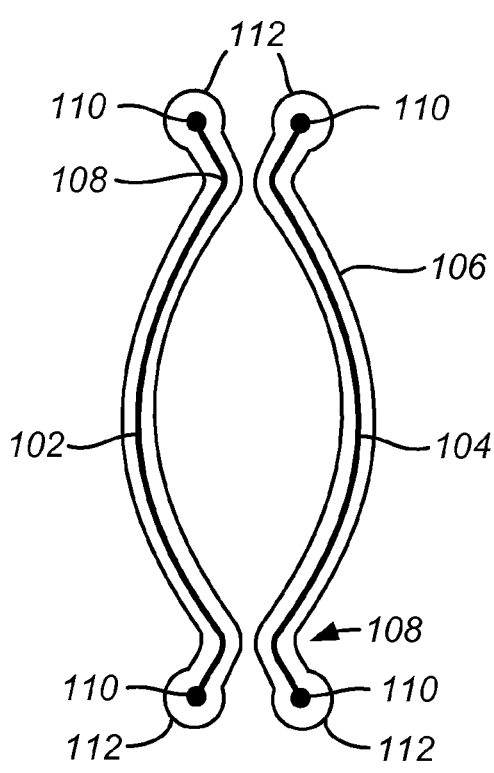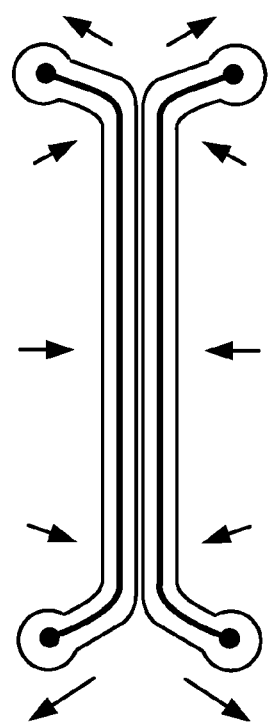
*FIG. 5H*     *FIG. 5I*

BIOPSY INCISION CLOSURE DEVICE

CROSS SECTION TO RELATED APPLICATIONS

This application is a continuation of Ser. No. 13/096,602, filed Apr. 28, 2011, which claims the benefit of the following provisional applications: Provisional Application No. 61/343,916, filed on May 3, 2010; Provisional Application No. 61/397,604, filed on Jun. 14, 2010; and Provisional Application No. 61/462,329, filed on Feb. 1, 2011, the full disclosures of which are incorporated herein by reference.

BACKGROUND OF THE INVENTION

1. Field of the Invention

The present invention relates generally to medical devices and methods. More particularly, the present invention relates to a device and method for closing a wound resulting from tissue biopsy.

Excisional biopsy typically removes an elliptical section of tissue, usually containing the full dermis and in some cases the subcutaneous fatty layer as well. Such biopsies typically leave an elliptical opening in the skin that requires closing. Such elliptical biopsy openings have been conventionally closed by suturing which places the skin on each side of the closure in tension. The edges of the skin must stretch in order for the previously separated incision edges to meet in the center. Typically, multiple, interrupted sutures or a running suture may be employed, both of which take significant physician time and often result in an unsightly scar. Additionally, such suturing techniques leave pathways through the skin through which pathogens can enter and cause infection.

For these reasons, it would be desirable to provide improved devices and methods for closing wounds resulting from tissue biopsy where the closure requires less time, provides a better aesthetic result, and lessens the risk of infection. At least some of these objectives will be met by the inventions described hereinbelow.

2. Description of the Background Art

Biopsy incision closure devices comprising an elliptical or oval base material which can be closed using an external clip or device are described in copending, commonly owned PCT Application PCT/US2010/00430, the full disclosure of which is incorporated herein by reference. Other relevant references include U.S. Pat. Nos. 3,933,158; 4,038,989; and 4,114,624; and US Published Application Numbers 2006/0200198; 2007/0088339; 2007/026078; 2008/0081951; 2008/0114396; and 2008/0287864.

BRIEF SUMMARY OF THE INVENTION

The present invention provides a biopsy incision closure device including a base having an opening and a tissue-adhering surface, and a frame incorporated in the base, where the frame has a first leg disposed along one side of the opening and a second leg disposed along an opposed side of the opening. The frame has a first configuration wherein the legs hold the opening in an elliptical shape through which the biopsy can be performed and a second configuration wherein the legs close the opening along generally straight lines. By "elliptical" it is meant that the opening is wider in the middle and generally tapered at each end. Thus, while the shape will often be that of a true ellipse, other tapered or fusiform geometries are also intended to be within the scope of the present invention.

In the exemplary embodiments, the frame is made of a material which is more rigid than the material of the base so that the frame distributes the closure forces more evenly along the opposed edges of a biopsy or other tissue cavity as the base is closed by the frame. Such even distribution of force can reduce or eliminate the point-load forces that are created by the use of discreet or running sutures, thus promoting faster and more uniform healing with minimal scarring.

The base will typically comprise a soft elastic or elastomeric material, such as silicone rubber, a polyurethane, and the like. In other embodiments, however, the base could comprise a woven fabric, optionally at least partially woven from elastic fibers or threads, or could be a laminated structure comprising two or more layers. In all instances, however, it is necessary that the base be able to elongate in at least the axial direction since the base will be axially elongated as the frame closes, as described in greater detail below. Often, the base will be isotropically elastic in all directions, but in other embodiments, the base may be anisotropically elastic so that the material of the base preferentially stretches in the axial direction and resists stretching in the lateral direction. As will be described below, the ability to resist stretching in the lateral direction is advantageous since it improves the traction applied to the tissue as the tissue is closed by the assembly of the frame and base.

At least a portion of a surface of the base which contacts the skin will be adapted to attach to the tissue surface to be closed, typically being covered with an adhesive to allow the base to be removably attached to the skin or other tissue surface. Suitable adhesives include acrylate-based adhesives, silicone rubber-based adhesives, and the like. In some instances, however, it may be desirable to alternatively or additionally attach the base to the skin or tissue surface using sutures, staples, fasteners, and the like, although such alternative or additional attachment will usually not be needed.

The frame will comprise a resilient material that is resistant to axial elongation (stretching) so that the legs of the frame can define the elliptical opening, maintain the peripheral dimension of the frame is opening, and move the edges of the elliptical opening in the base as the individual legs of the frame are moved toward one another. The frame may comprise a variety of hard, flexible plastics or metals, with an exemplary frame being formed from polyurethane. In an exemplary embodiment, the closure devices of the present invention may be formed by molding an elastomeric base material over a flexible plastic or metal frame. For example, metal wire or stamped metal frames could find use in addition to molded hard plastics.

The frame may be "self-opening" or "self-closing." Self-closing devices are closed when no biasing forces are applied to the frame. Since the legs are in the closed configuration, the physician typically opens the by axially compressing the ends of the frame to cause the legs to bow apart from each other. The frame and the base may then be attached to the skin or other tissue surface while the frame is held open by an amount judged by the doctor to be sufficient to perform the subsequent biopsy. While the legs will be biased to closing, usually the closure force is not sufficient to close the tissue after biopsy, and a further latching or other closure device will be needed to close the tissue opening, as described below.

More commonly, the frame is "self-opening" and in its elliptically open configuration when no biasing forces are applied to the frame. Such self-opening devices may be secured to the target skin or tissue surface without the need to axially compress the frame as needed with the previous embodiment. A latching or other closure mechanism will be used to close the frame as well as the elliptical opening in the base after the biopsy, as described in more detail below.

In certain embodiments, the biopsy incision closure devices of the present invention may further include a latching mechanism which can hold the legs in a closed or partially closed configuration, where the latching mechanism may be built into the frame or less commonly into the base itself. Often the latching mechanism will be adjustable so that the legs may be closed together at various spacings as desired by the physician. For example, the latching mechanism may comprise a ratchet member which extends between the first and second legs. In most instances, the latching member will be hinged to or otherwise connected with the frame of the closure device. In other embodiments, however, the ratchet mechanism or member could be separate from the frame and base of the closure device and inserted only after the biopsy has been completed.

Usually the legs of the frame will be joined together at their axial ends by hinges or hinge-like mechanisms. The hinges may take a variety of forms, and in the exemplary devices which are illustrated below, the hinges are either a keyhole or a living hinge. Other conventional hinges may be employed such as a ball and socket, a barrel and pin, a coil spring, or simple separate ball ends on the legs of the frame member, where the ball ends are embedded in the base or in another elastomeric block.

In a particularly useful embodiment, the hinge may comprise a leaf spring structure which applies an outward force to the tissue as the frame is closed. The outward force, in turn, can flatten the tissue at each end of the incision when the frame is closed, thus resisting tissue puckering and allowing the closure device to have a shorter length-to-width aspect ratio. Heretofore, biopsies have typically been performed with a relatively large length-to-width ratio in order to minimize deformation and scarring of the tissue at each end of the incision after the incision is closed. Providing a closure mechanism which can flatten the tissue at each end of the incision can reduce the need for excessively long incisions.

As mentioned above, the base needs to be able to stretch in the axial direction since the legs of the frame will elongate as the frame is closed. There is no corresponding need, however, for the base td stretch in a lateral dimension, and in fact it's preferable that stretching of the base material be limited in the lateral direction to improve the traction on the underlying tissue as the base and frame are closed. One way of achieving such selective stretchability is to employ an anisotropic material as the base or a portion of the base, where the material has a higher elasticity in an axial direction than in a lateral direction. Such anisotropic materials may comprise woven fabrics where the threads or fibers in one direction are elastic while in the other direction are inelastic. Alternatively, fabrics made entirely of an elastic material can be reinforced (by inelastic fibers, wire, threads, or other elements) in only a single (lateral) direction in order to achieve the desired anisotropticity.

In the exemplary embodiments below, however, the anisotropic stretching of the base is achieved by providing reinforcement members projecting laterally outwardly from the legs of the frame. Such reinforcement members are embedded in the base material and inhibit stretching in the lateral direction while allowing the stretching in the axial direction.

The reinforcement members may provide structural benefits as well. The members may minimize unwanted tissue inversion effects which could result from torque applied to the legs of the frame by the closing mechanism. Since the latch mounts above the skin, a moment arm is created wherever the latch(es) attaches to the device which can twist the mounting point and the frame resulting in inverted incision edges. The "spider leg" geometry of the reinforcement members can act as a struts or ribs to counteract this torque because they convert torque forces into normal forces (perpendicular to the skin plane) under each reinforcement member. Since the reinforcement member extends relatively far from the incision, twisting of the frame and subsequent wound inversion is inhibited.

In an additional aspect, the present invention can provide biopsy closure devices which can evert the edges of the tissue as they are brought together in order to improve healing. In such embodiments, an eversion lip will be provided along the edges of the first and second legs of the frame so that the lips engage the tissue and extend inwardly from the elliptical periphery of the frame when present on the tissue. The eversion lip is attached to the frame with a living hinge or otherwise so that it will evert upwardly as the frame is closed, thus lifting the tissue to provide the desired tissue edge eversion. Such tissue eversion promoting may also be achieved by deflecting the frame legs so that they are "normally" in a lifted state, so that when the base is adhered to the skin (it must be pressed down a bit to fully contact the skin), the upwardly deflected inner portions of the base will lift the skin slightly to promote eversion upon closure. This approach may be in addition to or an alternative to the hinged approach described above.

The present invention further provides methods for biopsying tissue. A base having an opening is adhered to a tissue surface, where the base includes a resilient frame which surrounds the opening. The tissue is excised through the opening, leaving a cavity having opposed, laterally spaced-apart edges in the tissue. The frame is then closed to apply a generally uniform distribution of lateral closing forces along opposite of the opening to evenly close the edges of tissue along the cavity. Usually, the opening in the base will be elliptical, as defined above, and the frame will be closed using a latching mechanism of the type described above. Optionally, prior to adhering the base to the tissue surface, the frame may be open by axially compressing the ends of the frame. The base may preferentially stretch in an axial direction to accommodate elongation of the cavity as the opposite sides are closed in a lateral direction, and typically the base is inhibited from stretching in the lateral direction by reinforcing elements on the frame or otherwise disposed in the base itself.

In the specific embodiments, the frame is closed by advancing a ratchet from one side of the frame to a laterally opposite side of the frame. As the frame closes, the hinge or other mechanism at either both axial ends may apply an outward force to flatten the tissue in order to reduce tissue deformation during healing. The frame may also comprise a lip configured to raise an inner periphery of the base opening to evert the tissue adhered to the base as the frame is closed.

BRIEF DESCRIPTION OF THE DRAWINGS

FIGS. 5A-5I illustrate different hinge structures which may be used to attach the axial ends of the leg members of the frames of the present invention.

DETAILED DESCRIPTION OF THE INVENTION

Figure 1A:
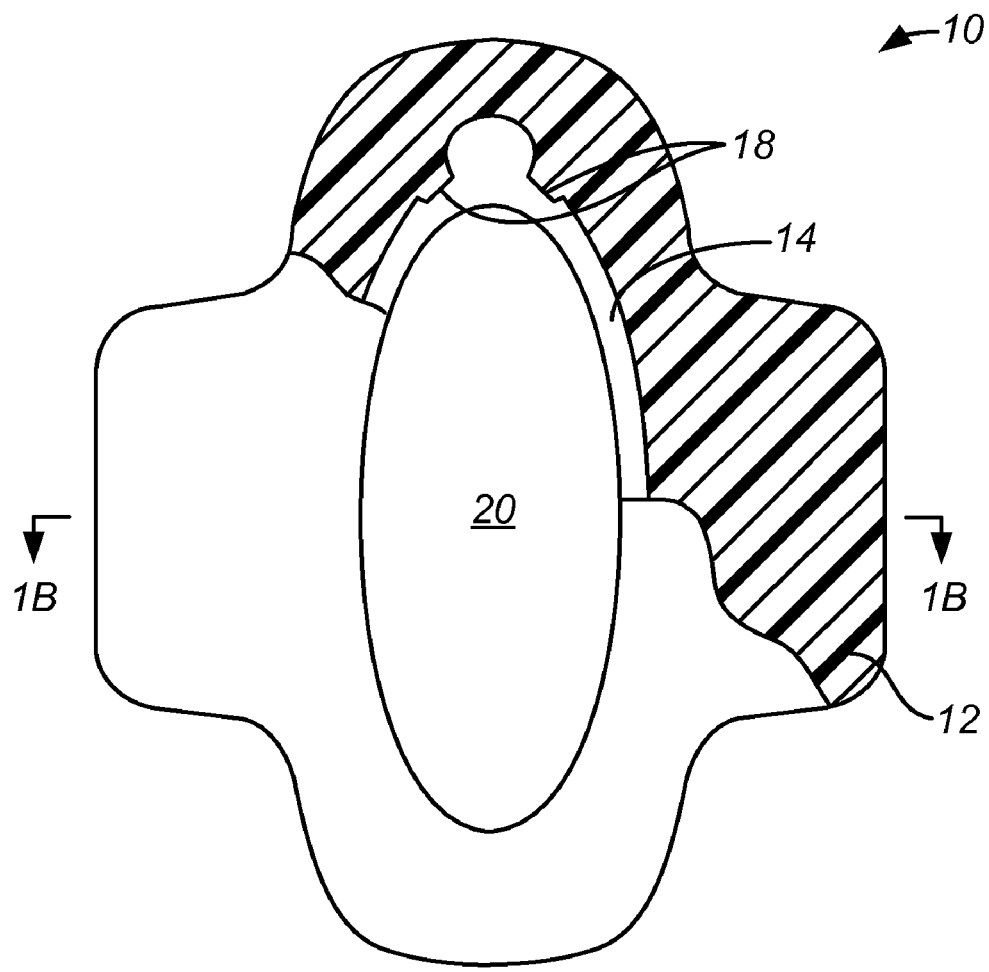
FIGS. 1A-1D illustrate a first embodiment of a biopsy incision closure device constructed in importance with the principles of the present invention.
Figure 1B:
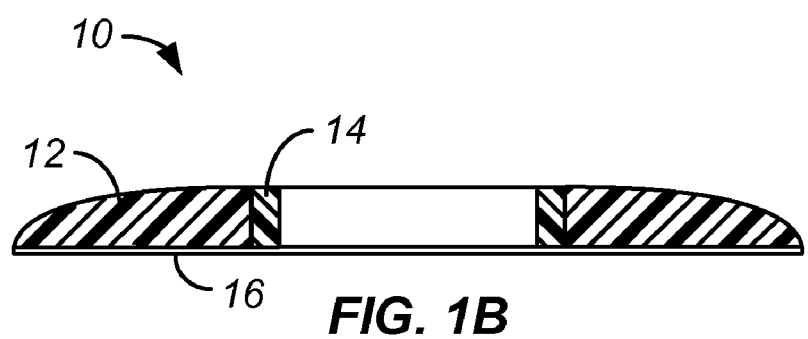
Figure 1C:
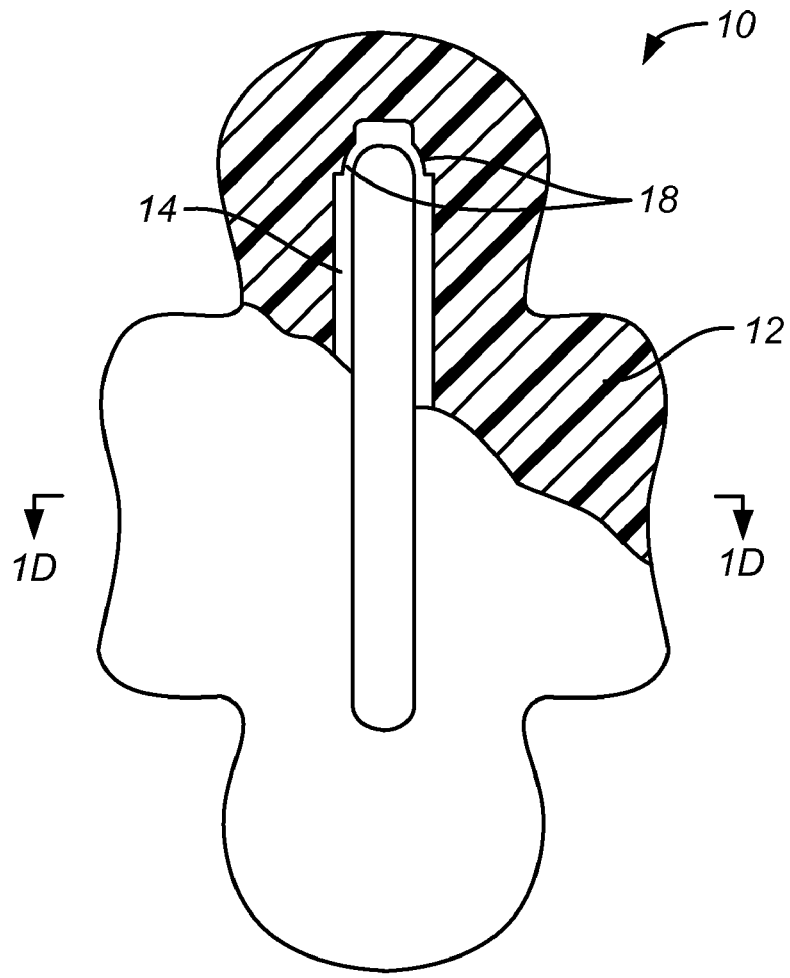
Figure 1D:
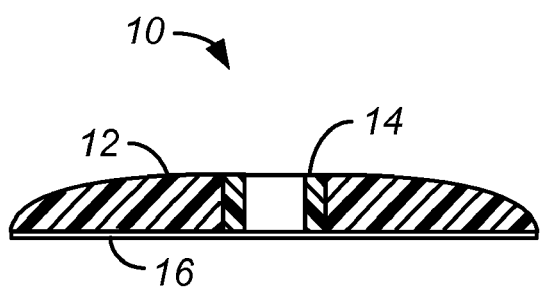

Referring to FIGS. 1A through 1D, a biopsy incision closure device 10 comprises a base 12 having an integrated or embedded frame 14, typically formed by overmolding a soft polymeric base material over a preformed metal or hard plastic frame. The frame 14 is resilient and, when free from biasing forces, assumes the elliptical or oval configuration seen in FIG. 1A. The frame 14 has living hinges 18 at each end (only one of which is visible in the broken-away section of the base) which allow the base to be closed by applying laterally inward forces to the frame, as shown in FIGS. 1C and 1D. Laterally inward forces may be provided by any one of a variety of external closure devices which could be simple tapes, patches, sutures, or the like. Closure devices could be more complex, including zippers, clips, and other structures as taught in copending PCT Application PCT/US2010/00430, the full disclosure of which has been previously incorporated herein by reference. Regardless of the particular mechanism used for closing, the opposed legs of the frame 14 can be brought from their curved or arcuate (arched) configuration on the frame and base are free from vising forces, as shown in FIGS. 1A and 1B, to a generally straight configuration as shown in FIGS. 1C and 1D. Such straight closure is advantageous for closing elliptical biopsy cavities as described in more detail below.

The frame defines an opening 20 in the base which is available for performing the biopsy after the device 10 has been adhered to a target tissue surface, typically using an adhesive layer 16 on a bottom surface of the base and frame, as best seen in FIGS. 1B and 1D.

Figure 2A:
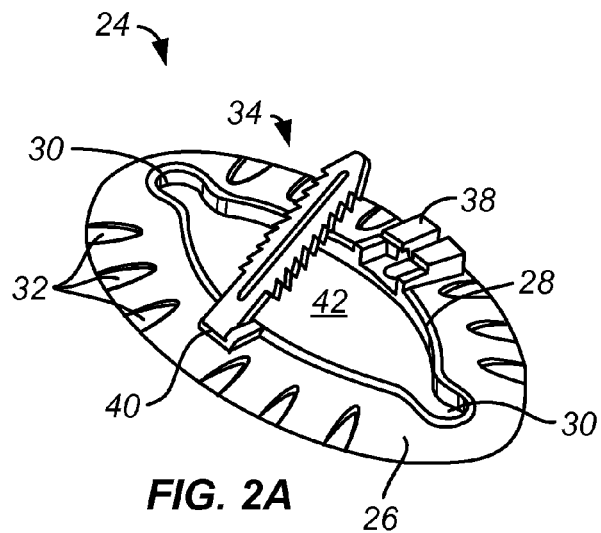
FIGS. 2A-2D illustrate a second embodiment of a biopsy incision closure device constructed in accordance with the principles of the present invention, and including an integrated latching mechanism.
Figure 2B:
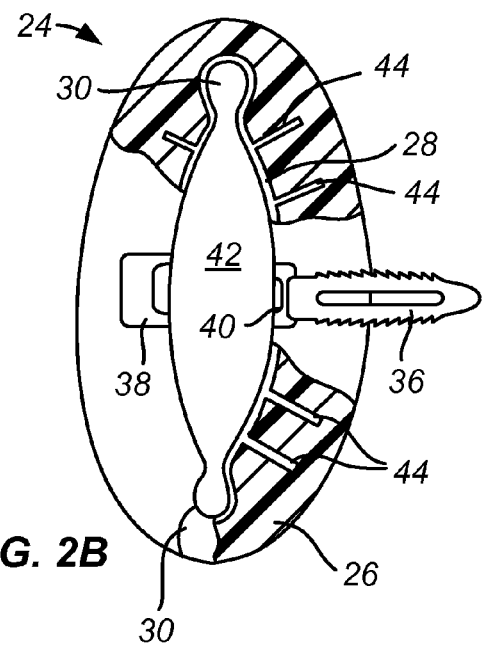
Figure 2C:
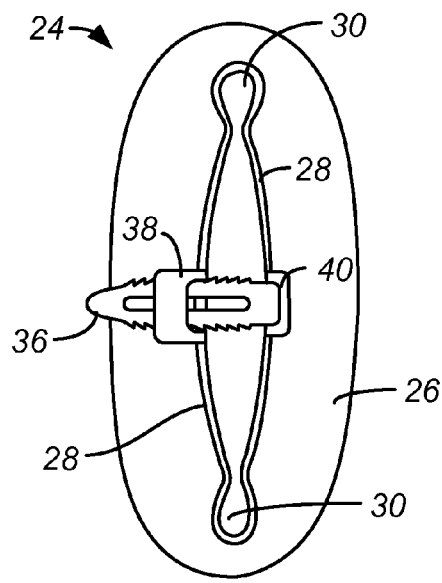
Figure 2D:
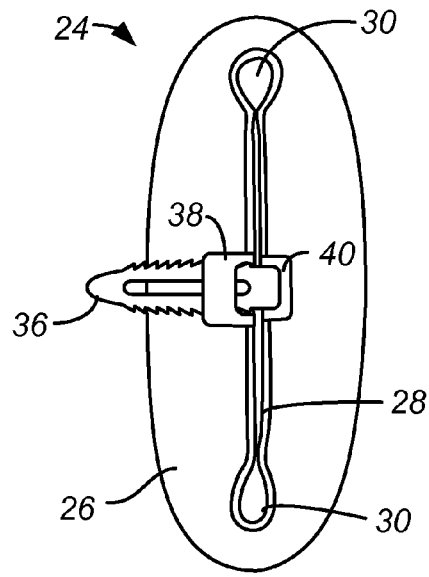

A second biopsy incision closure device 24 is illustrated in FIGS. 2A-2D. The closure device 24 includes a base 26 and frame 28, similar to the device 10, but differs from the device 10 in that device 24 includes a latch mechanism 34 for effecting closure as will be described below. Other differences include the use of keyhole hinges 30 at the axial ends of each leg of the frame 28 and the presence of cut outs 32 around the perimeter of the base 26. The cut outs further increase the axial elasticity of the base and allow it to both stretch and conform to the tissue as the frame closes and the base elongates, as shown in FIGS. 2C and 2B (although the cut outs 32 are not shown in those figures). The base 26 and frame 28 together define an elliptical opening 42 which is fully open when ratchet number 36 of the latching mechanism 34 is open, as shown in FIGS. 2A and 2B. By closing the ratchet member 36, as shown in FIG. 2C, into a coupler 38 on the opposite leg of the frame 28, the physician may close the opening 42 by pressing laterally inwardly or "squeezing" the frame 28 to cause the ratchets of ratchet member 36 to move through the coupler 38. Thus, the frame 28 and base 26 can be partially closed, as shown in FIG. 2C, or fully closed as shown in FIG. 2D, depending on the desires of the physician. Although not shown, the base 26 will typically have an adhesive on the surface which engages tissue, although an adhesive could be separately applied to the tissue or other attachment devices, such as sutures or staples could be used.

A further difference in the device 24 is that it includes a plurality of reinforcement members 44 (FIG. 2B) which project laterally outwardly from the legs of the frame 28. These reinforcement numbers are embedded in the base material in order to provide for lateral reinforcement to inhibit lateral stretching of the base material as the legs are closed as well as to inhibit inward twisting of the legs of the frame.

Figure 3:
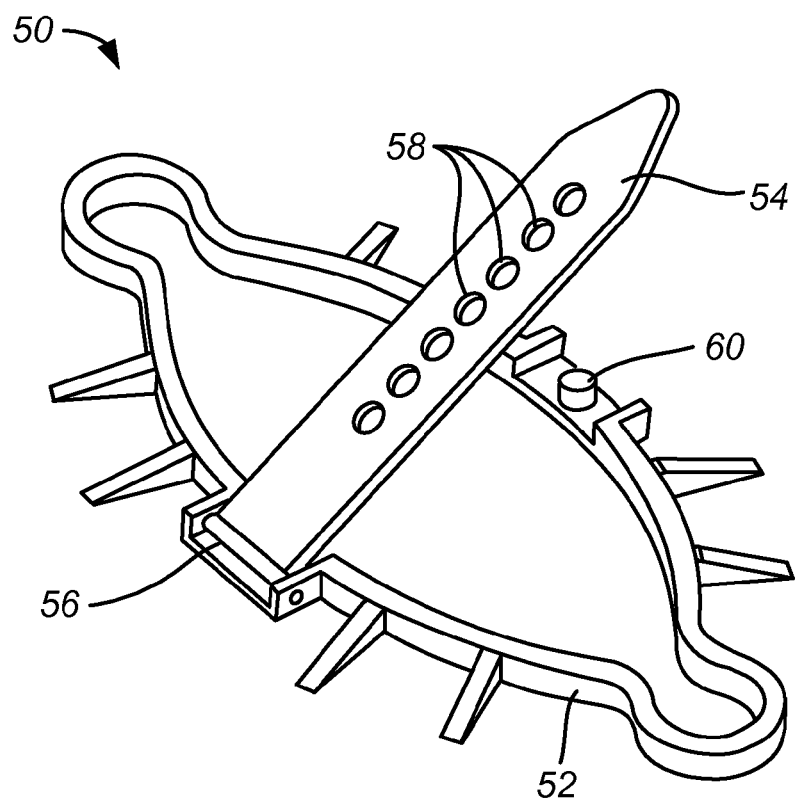
FIG. 3 illustrates a frame member incorporating an alternative embodiment of a latching mechanism.

An alternative latching mechanism 50 is shown on a frame 52 in FIG. 3. The latching mechanism 50 does not include a ratchet but instead includes an arm 54 attached by a hinge 56 and having a plurality of holes 58 along its length. The holes 58 may be snapped over pin 60, with each individual hole representing a different closure spacing for the legs of the frame 52.

Figure 4:
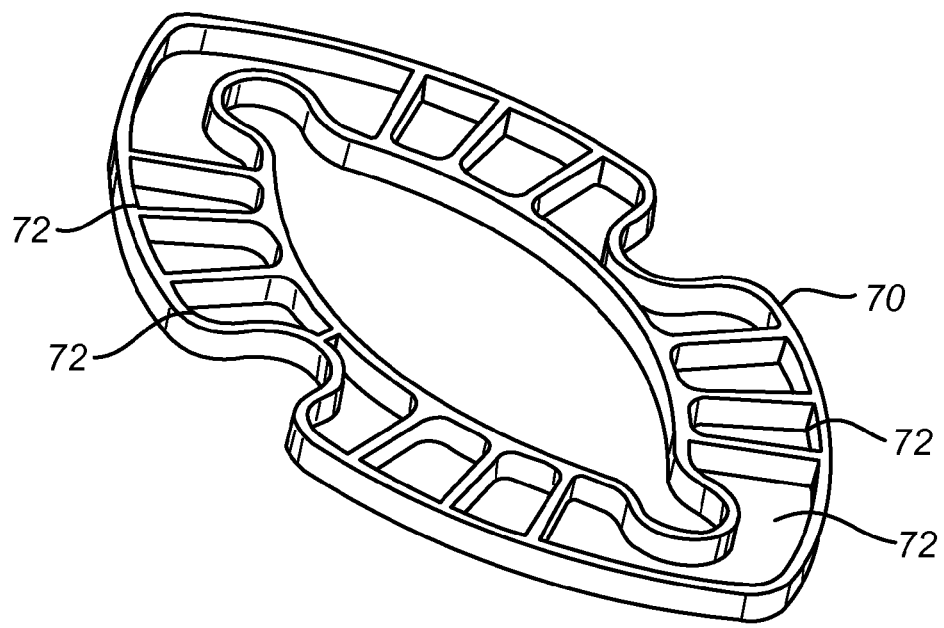
FIG. 4 illustrates an alternative frame design without a latching mechanism.

An alternative frame structure 70 is shown in FIG. 4 where the frame is not a simply elliptically shaped element but instead comprises a plurality of cells 72 which together form an elliptical scaffold for incorporation in the elastomeric or other base. This structure can improve the adherence when the frame is overmolded with the base material.

Figure 5A:
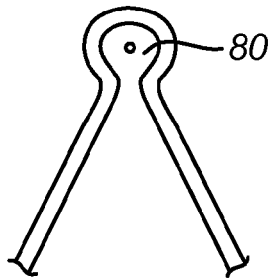
Figure 5B:
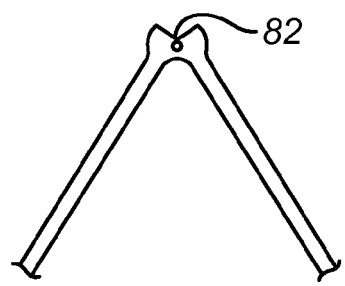
Figure 5C:
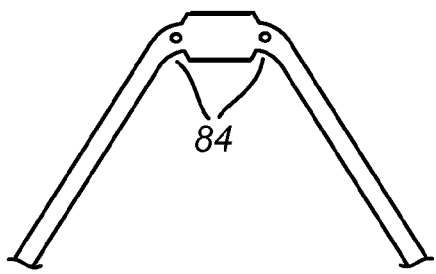
Figure 5D:
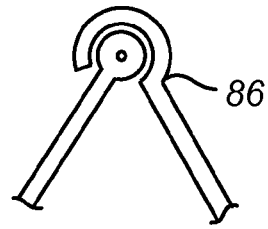
Figure 5E:
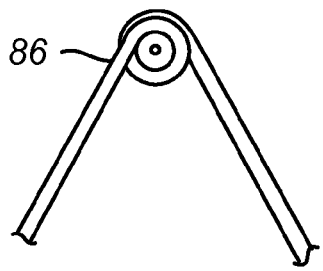
Figure 5F:
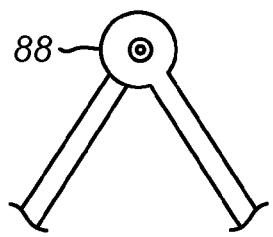
Figure 5G:
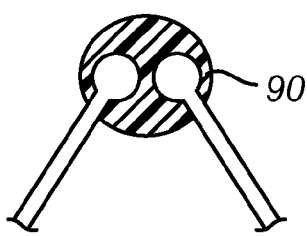

Referring now to FIGS. 5A through 5G, in addition to a simple keyhole hinge 80 (FIG. 5A) and simple living hinge 82 (FIG. 5B), individual legs of the frame maybe joined by a variety of other hinge structures. For example, the double living hinge 84 is illustrated at FIG. 5C and a ball and socket hinge 86 is illustrated in FIG. 5D. A coil spring hinge 86 is illustrated in FIG. 5E and a pivoted hinge 88 is illustrated in FIG. 5F. The ends of the legs of the frame need not be directly in contact and can instead be connected by a third element, such as an elastomeric matrix 90 as shown in FIG. 5G.

FIGS. 5H and 5I illustrate a particularly useful hinge configuration for the individual legs of the frame of the present invention. As shown in FIG. 5H, individual legs 102 and 104 of a frame and a base 106 can be loosely attached in a "scissored" or "leaf spring" configuration 108 at each end. The legs then extend to outwardly flared tips 110 and individual pods 112 of the base which can be attached to tissue in the configuration as shown in FIG. 5H. As the closure device at FIG. 5A is closed, as shown in FIG. 5I, the central portion of the closure device will apply laterally inward forces as shown by the arrows, while the pod elements 112 at each end will apply laterally outward forces as shown by the arrows at those end. Such as a "leaf spring" frame structure both closes the incision to a vertical line, as shown in FIG. 5I, and also provide for outward movement of the tissue at the ends which will flatten the tissue and improve healing.

Figure 6:
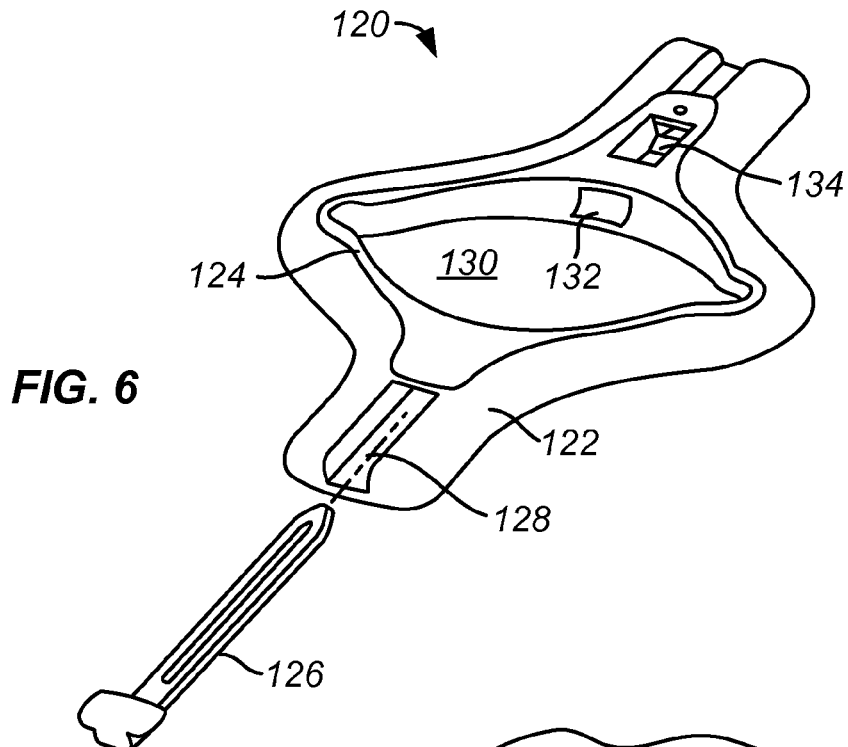
FIG. 6 illustrates yet another embodiment of the biopsy incision enclosure device of the present invention incorporating a separate, unattached ratchet closure device.

Referring now to FIG. 6, yet a further embodiment of a biopsy incision closure device 120 is illustrated. The closure device 120 includes a base 122 and frame 124 having different configurations but serving the same purposes as described in the previous embodiments. The most significant difference with device 120 is that a latch element 126 is formed as a separate piece, i.e., it is not attached to the frame or to the base. Latch element 126 will typically have a ratcheting structure (not shown) and can be inserted through an insertion channel 128, across the opening 130 and into an aperture 132 which is adjacent a ratcheting closure mechanism 134.

In yet another aspect of the present invention, it will often be desirable to precisely form a biopsy along an incision line which is based slightly inwardly from the periphery of the opening defined by the frame. To do so, a template 140 may be inserted into opening 142 of any one of the biopsy closure devices, shown generically as closure device 144. By then drawing a line around the inner periphery of the template 140, removing the template, and cutting along the drawn line, a precisely defined tissue cavity will be formed. The closure device will then close the incision with small marginally or peripheral edges of the tissue being brought together to optimally compress and close the wound.

Figure 8A:
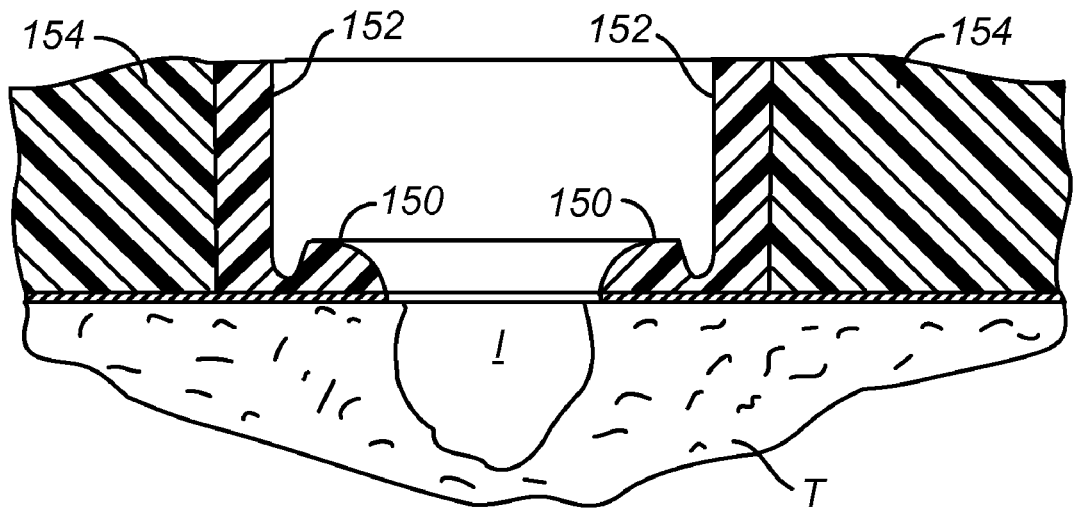
FIGS. 8A and 8B illustrate everting lips on the frame in order to raise tissue as the frame is closed.
Figure 8B:
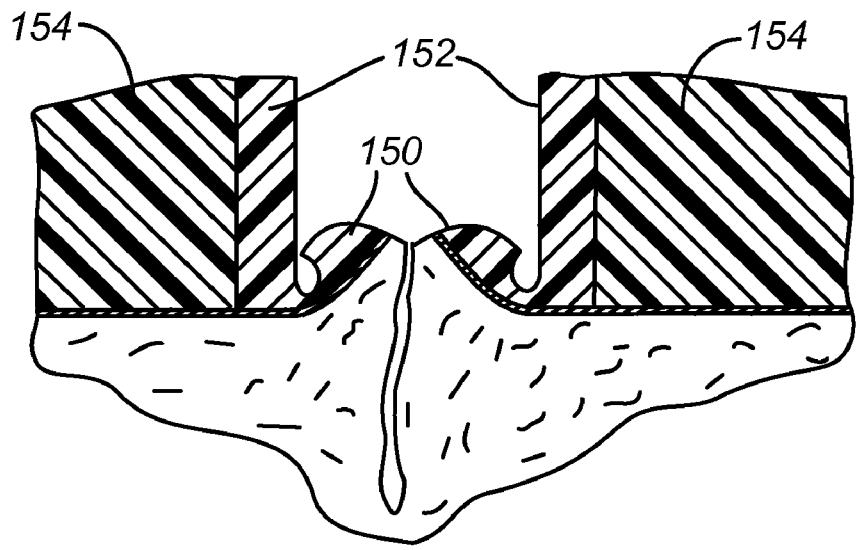

Referring now to FIGS. 8A and 8B, an alternative mechanism for improving the tissue apposition is illustrated. Everting rails 150 maybe formed at the base of individual legs 152 and a closure device having a base 154. After an incision 1 is formed in the tissue T, the legs 152 will be closed as describe above, causing the everting rails 150 to rise and raise the edges of the tissue, as shown in FIG. 8B. Such raised tissue edges can improve the healing and reduce any cavities remaining below the surface of the tissue.

Figure 7B:
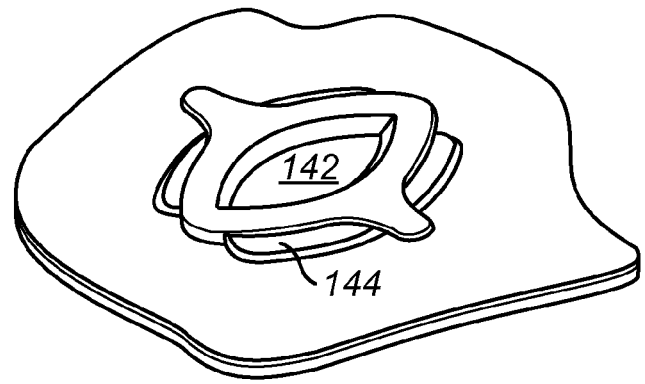
FIGS. 7A and 7B illustrate use of a template for marking an elliptical or fusiform opening before biopsy.
Figure 7A:
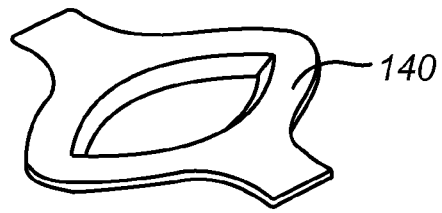
Figure 9A:
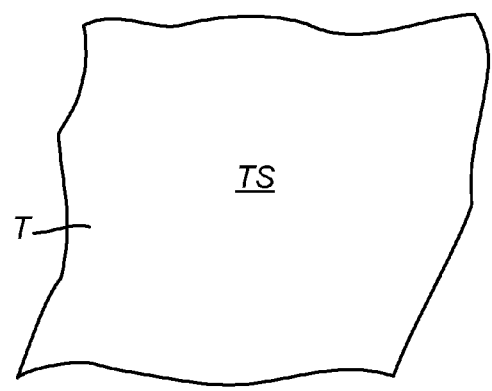
FIGS. 9A through 9D illustrate use of the biopsy incision closure device of FIGS. 2A-2E for taking a biopsy and subsequently closing the biopsy cavity in accordance with the principles of the present invention.
Figure 9B:
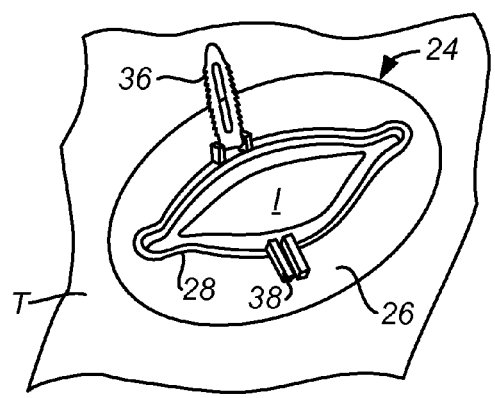
Figure 9C:
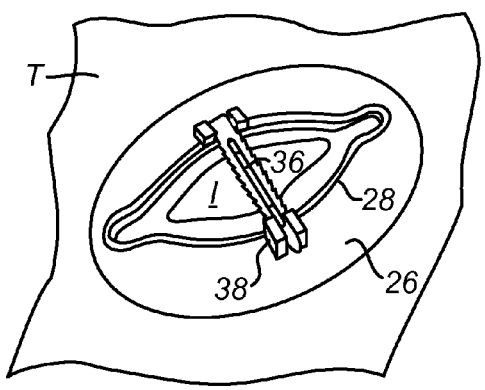
Figure 9D:
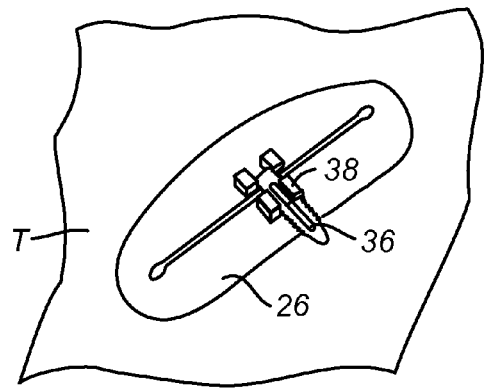

Referring now to FIGS. 9A through 9B, use of the biopsy incision closure device 24 illustrated in FIGS. 2A through 2D for forming and closing a biopsy incision will be described. As shown in FIG. 9A, a target site TS is identified in a tissue surface T. The device 24 is then placed over the target site TS with the opening in the device generally symmetrically placed over the site. Optionally, the template 140 FIG. 7A is used to draw an incision line, and then an incision is cut or then the opening of the device 24, shown in FIG. 9B. After the tissue is removed from the incision, the ratchet member 36 is closed and inserted in the coupler 38, as illustrated in FIG. 9C. Physician can then squeeze the opposed legs of the frame 28 together so that the ratchet member 36 advances from the coupler 38 and eventually closes the tissue to the extent desired by the physician, as shown in FIG. 9D. The closure device can then be left in place for time sufficient for the wound to heal.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A biopsy incision closure device comprising:
 a base having an opening; and
 a frame incorporated in the base, the frame having a first leg disposed along one side of the opening and a second leg disposed along an opposed side of the opening;
 wherein the frame has a first configuration wherein the legs hold the opening in an elliptical shape through which the biopsy can be performed and a second configuration wherein the legs close or partially close the opening, wherein the frame comprises a hard, flexible plastic or metal and the base comprises a soft elastomeric material molded over the frame, and wherein the base has a bottom surface coated with an adhesive and the opening is formed through the bottom surface.

2. A biopsy incision closure device as in claim 1, wherein the elastomeric material is selected from the group consisting of silicone rubber.

3. A biopsy incision closure device as in claim 1, wherein the base comprises two or more laminated layers.

4. A biopsy incision closure device as in claim 1, wherein the frame is in a closed leg configuration when no biasing forces are applied to the frame.

5. A biopsy incision closure device as in claim 4, wherein the frame is opened by axially compressing the first and second legs which causes them to deform into the elliptical shape, wherein a user can adjust the size of the opening by varying the amount of axial compression.

6. A biopsy incision closure device as in claim 1, wherein the frame is in an open leg configuration when no biasing forces are applied to the frame.

7. A biopsy incision closure device as a claim 6, further comprising a latching mechanism which hold the legs in a closed or partially closed configuration.

8. A biopsy incision closure device as in claim 7, wherein the latching mechanism is adjustable to hold the legs together at varying spacings there between.

9. A biopsy incision closure device as in claim 8, wherein the latching mechanism comprises a ratchet member which extends between the first leg and the second leg.

10. A biopsy incision closure device as in claim 1, wherein the legs are joined together at each end by hinges.

11. A biopsy incision closure device as in claim 10, wherein each hinge comprises a keyhole.

12. A biopsy incision closure device as in claim 10, wherein each hinge comprises a leaf spring structure which applies an outward force which flattens the tissue at each end of an incision when the frame is closed.

13. A biopsy incision closure device as in claim 10, wherein each hinge comprises a living hinge, a ball and socket, a barrel and pin, a coil spring, or ball ends embedded in the base.

14. A biopsy incision closure device as in claim 1, wherein the base stretches preferentially in the axial direction.

15. A biopsy incision closure device as in claim 14, wherein the base comprises an anisotropic material which has a higher elasticity in the axial direction than in a lateral direction.

16. A biopsy incision closure device as in claim 14, wherein the base comprises a material with isotropic elastic properties, wherein the isotropic material is reinforced to inhibit stretching in a lateral direction while allowing uninhibited stretching in the axial direction.

17. A biopsy incision closure device as in claim 16, wherein the frame comprises lateral reinforcement elements which inhibit lateral stretching of the base.

18. A biopsy incision closing device as in claim 1, further comprising an eversion lip along each of the first and second legs of the frame, wherein the eversion lip is oriented to adhere to tissue within the opening and to deflect upwardly as the frame is closed to evert edges of the tissue upwardly.

* * * * *

UNITED STATES PATENT AND TRADEMARK OFFICE
CERTIFICATE OF CORRECTION

PATENT NO. : 8,313,508 B2  
APPLICATION NO. : 13/286378  
DATED : November 20, 2012  
INVENTOR(S) : Amir Belson et al.

Page 1 of 1

It is certified that error appears in the above-identified patent and that said Letters Patent is hereby corrected as shown below:

Title page, Related U.S. Application Data (60), the priority claims to "Provisional application No. 61/343,916, filed on May 6, 2010, provisional application No. 61/397,604, filed on Jun. 14, 2010, provisional application No. 61/462,329, filed on Feb. 1, 2011." should be changed to --"Provisional application No. 61/343,716, filed on May 3, 2010, provisional application No. 61/397,604, filed on Jun. 14, 2010, provisional application No. 61/462,329, filed on Feb. 1, 2011."--

Specification

Column 1, lines 5 to 11, "This application is a continuation of Ser. No. 13/096,602, filed Apr. 28, 2011, which claims the benefit of the following provisional applications: Provisional Application No. 61/343,916, filed on May 3, 2010; Provisional Application No. 61/397,604, filed on Jun. 14, 2010; and Provisional Application No. 61/462,329, filed on Feb. 1, 2011, the full disclosures of which are incorporated herein by reference." should be changed to --"This application is a continuation of Ser. No. 13/096,602, filed Apr. 28, 2011, which claims the benefit of Provisional Application No. 61/397,604, filed on Jun. 14, 2010, and Provisional Application No. 61/462,329, filed on Feb. 1, 2011, the full disclosures of which are incorporated herein by reference; and, Ser. No. 13/096,602 also claims the benefit of Provisional Application No. 61/343,716, filed May 3, 2010."--

Signed and Sealed this  
Twelfth Day of January, 2016

Michelle K. Lee  
*Director of the United States Patent and Trademark Office*